(12) United States Patent
Tabata et al.

(10) Patent No.: US 10,092,582 B2
(45) Date of Patent: Oct. 9, 2018

(54) CELL MOBILIZATION AGENT CONTAINING LYSOPHOSPHOLIPID WITH RETINOIC ACID INTRODUCED

(71) Applicants: NOF CORPORATION, Tokyo (JP); Yasuhiko Tabata, Uji-shi, Kyoto (JP)

(72) Inventors: Yasuhiko Tabata, Uji (JP); Kohei Yoshimura, Kawasaki (JP)

(73) Assignees: NOF CORPORATION, Tokyo (JP); Yasuhiko Tabata, Uji (JP)

(*) Notice: Subject to any disclaimer, the term of this patent is extended or adjusted under 35 U.S.C. 154(b) by 0 days.

(21) Appl. No.: 15/320,695

(22) PCT Filed: Jun. 22, 2015

(86) PCT No.: PCT/JP2015/067851
§ 371 (c)(1),
(2) Date: Dec. 20, 2016

(87) PCT Pub. No.: WO2015/199020
PCT Pub. Date: Dec. 30, 2015

(65) Prior Publication Data
US 2017/0157154 A1 Jun. 8, 2017

(30) Foreign Application Priority Data
Jun. 23, 2014 (JP) .................. 2014-128644

(51) Int. Cl.
*A61K 31/685* (2006.01)
*A61K 47/34* (2017.01)
*A61K 47/36* (2006.01)
*A61K 47/42* (2017.01)

(52) U.S. Cl.
CPC ......... *A61K 31/685* (2013.01); *A61K 47/34* (2013.01); *A61K 47/36* (2013.01); *A61K 47/42* (2013.01)

(58) Field of Classification Search
CPC .................................................. A61K 31/685
See application file for complete search history.

(56) References Cited

U.S. PATENT DOCUMENTS

| | | | |
|---|---|---|---|
| 4,882,165 A | 11/1989 | Hunt et al. | |
| 5,776,915 A | 7/1998 | Peterson et al. | |
| 5,985,292 A | 11/1999 | Fourneron et al. | |

FOREIGN PATENT DOCUMENTS

| | | |
|---|---|---|
| JP | H07-188280 A | 7/1995 |
| JP | H07-206879 A | 8/1995 |
| JP | 2002-514183 A | 5/2002 |
| WO | WO 1998/011906 A1 | 3/1998 |
| WO | WO 2000/024750 A1 | 5/2000 |

OTHER PUBLICATIONS

Pidgeon et al. Methods in Enzymology, 1987, vol. 149, pp. 99-111.*
Gude et al., "Apoptosis induces expression of sphingosine kinase 1 to release sphingosine-1-phosphate as a 'come-and-get-me' signal," *The FASEB Journal*, 22(8): 2629-2638 (2008).
Peter et al., "Migration to Apoptotic 'Find-me' Signals Is Mediated via the Phagocyte Receptor G2A," *The Journal of Biological Chemistry*, 283(9): 5296-5305 (2008).
Pidgeon et al., "Light Sensitive Liposomes," *Photochemistry and Photobiology*, 37(5): 491-494 (1983).
Velnar et al., "The Wound Healing Process: an Overview of the Cellular and Molecular Mechanisms," *The Journal of International Medical Research*, 37(5): 1528-1542 (2009).
Japanese Patent Office, International Search Report in International Patent Application No. PCT/JP2015/067851 (dated Sep. 29, 2015).
Japanese Patent Office, International Preliminary Report on Patentability in International Patent Application No. PCT/JP2015/067851 (dated Dec. 27, 2016).
Frasch et al., "Lysophospholipids of Different Classes Mobilize Neutrophil Secretory Vesicles and Induce Redundant Signaling through G2A," *J. Immunol.*, 178(10): 6540-6548 (2007).
European Patent Office, Extended European Search Report in European Patent Application No. 15812300.0 (dated Jan. 8, 2018).

* cited by examiner

*Primary Examiner* — James D. Anderson
(74) *Attorney, Agent, or Firm* — Leydig, Voit & Mayer, Ltd.

(57) ABSTRACT

The invention provides a cell mobilizing agent capable of efficiently and continuously accumulating cells involved in tissue repair. In particular, the cell mobilizing agent contains a lysophospholipid introduced with retinoic acid represented by the formula (1) and/or the formula (2) or a physiologically acceptable salt thereof as an active ingredient:

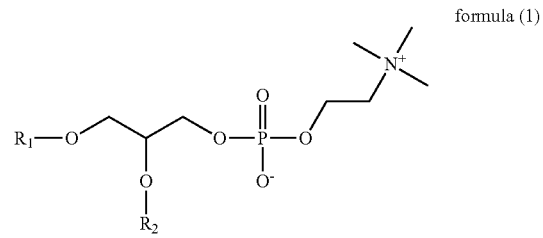

formula (1)

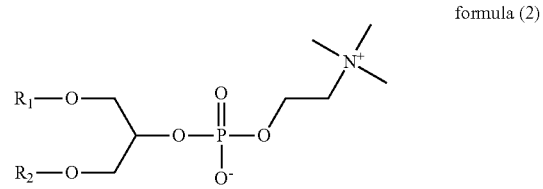

formula (2)

wherein $R_1$ and $R_2$ are each a retinoyl group or hydrogen and are not the same.

12 Claims, 4 Drawing Sheets

CELL MOBILIZATION AGENT CONTAINING LYSOPHOSPHOLIPID WITH RETINOIC ACID INTRODUCED

CROSS-REFERENCE TO RELATED APPLICATIONS

This patent application is the U.S. national phase of International Patent Application No. PCT/JP2015/067851, filed on Jun. 22, 2015, which claims the benefit of Japanese Patent Application No. 2014-128644, filed on Jun. 23, 2014, the disclosures of which are incorporated herein by reference in their entireties for all purposes.

TECHNICAL FIELD

The present invention relates to a cell mobilizing agent containing a lysophospholipid introduced with retinoic acid.

BACKGROUND ART

It is known that the actions of neutrophils, eosinophils, monocytes, macrophages, and the like, which are blood cells, are involved in the tissue repair processes such as wound healing, degeneration of tumor and the like. Among these, macrophages play an important role in the tissue repair, such as promotion of wound healing by phagocytosis of dead cells and foreign substances that invaded into the living body and production of growth factors etc., and the like.

Therefore, if migration and accumulation, i.e., mobilization, of blood cells, particularly macrophages, to the targeted diseased part can be performed by some method, promotion of tissue repair is expected. Since macrophages are cells differentiated after mobilization of monocytes present in blood to each tissue, it is also possible to promote tissue repair by accumulating monocytes (non-patent document 1).

As a biological substance capable of mobilizing monocytes and macrophages, 1-stearoyl-lysophosphocholine (C18:0-LysoPC), sphingosine-1-phosphoric acid (S1P) and the like, which belong to one kind of lysophospholipid, have been reported (non-patent documents 2, 3). Since monocytes and macrophages recognize concentration gradients of these substances and have the property of being mobilized to concentrated parts, promotion of tissue repair requires an increase in the local concentration. Also, promotion of tissue repair requires continuous mobilization of monocytes and macrophages. However, C18:0-LysoPC exhibits an effect only in a high concentration condition of 10 µM or more, and side effects such as cytotoxicity and the like may occur under higher concentration conditions. On the other hand, SiP exhibits an effect at a lower concentration than C18:0-LysoPC by acting on SiP receptor 1. However, when the concentration is 100 nM or more, it suppresses mobilization of monocytes and macrophages by acting on SiP receptor 2. As a result, the effective concentration range of SiP is extremely narrow and around 10 nM. Furthermore, when it is administered to a living body, the topical lysophospholipid concentration decreases due to blood flow, in addition to a simple diffusion phenomenon, which necessitates intermittent topical administration to maintain the above-mentioned effective concentration. As a result, the quality of life (QOL) is degraded and the treatment costs increase.

DOCUMENT LIST

Non-Patent Documents non-patent document 1: The Journal of International Medical Research. 37, 1528-1542 (2009)

non-patent document 2: The Journal of Biological Chemistry. 283, 5296-5305 (February 2008)

non-patent document 3: The FASEB Journal. 22, 2629-2638 (August 2008)

SUMMARY OF THE INVENTION

Problems to be Solved by the Invention

An object of the present invention is to provide a cell mobilizing agent capable of efficiently and continuously accumulating cells involved in tissue repair. Also, an object of the present invention is to provide a cell mobilizing agent capable of reducing side effects and not requiring intermittent topical administration.

Means of Solving the Problems

The present inventors have conducted intensive studies in an attempt to solve the aforementioned problems and found that lysophospholipids introduced with retinoic acid represented by the below-mentioned formulas (1) and (2) and a physiologically acceptable salt thereof (hereinafter sometimes to be abbreviated as "Ret-LysoPC") have an effect of mobilizing cells, involved in tissue repair, under wide concentration range. Based on the finding, they have conducted further studies and completed the present invention.

The present invention provides the following.

[1] A cell mobilizing agent comprising a lysophospholipid introduced with retinoic acid represented by the formula (1) is and/or the formula (2) or a physiologically acceptable salt thereof as an active ingredient:

wherein, $R_1$ and $R_2$ are each a retinoyl group or hydrogen and are not the same with each other.

[2] The cell mobilizing agent of the above-mentioned [1], wherein the retinoyl group is all-trans form, 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, 9,11,13-tri-cis form or all-cis form.

[3] The cell mobilizing agent of the above-mentioned [1] or [2], which is for promoting biological tissue repair by cell mobilization.

[4] The cell mobilizing agent of any of the above-mentioned [1]-[3], wherein the cell to be mobilized is a blood cell, a hematopoietic stem cell or a mesenchymal stem cell.

[5] The cell mobilizing agent of any of the above-mentioned [1]-[4], which is a sustained-release preparation comprising a sustained release substrate.
[6] The cell mobilizing agent of the above-mentioned [5], wherein the sustained release substrate is a biodegradable polymer.
[7] The cell mobilizing agent of the above-mentioned [6], wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof and crosslinked forms thereof.

The present invention also relates to the following.

[8] A biological tissue repair promoter comprising a lysophospholipid introduced with retinoic acid represented by the formula (1) and/or the formula (2) or a physiologically acceptable salt thereof as an active ingredient:

wherein, $R_1$ and $R_2$ are each a retinoyl group or hydrogen and are not the same with each other.
[9] The biological tissue repair promoter of the above-mentioned [8], wherein the retinoyl group is all-trans form, 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, 9,11,13-tri-cis form or all-cis form.
[10] The biological tissue repair promoter of the above-mentioned [8] or [9], which is a sustained-release preparation further comprising a sustained release substrate.
[11] The biological tissue repair promoter of the above-mentioned [10], wherein the sustained release substrate is a biodegradable polymer.
[12] The biological tissue repair promoter of the above-mentioned [11], wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof and crosslinked forms thereof.

Effect of the Invention

The present invention enables continuous accumulation of cells involved in tissue repair. For example, the cells involved in the tissue repair can be continuously accumulated on an affected part (e.g., joints, skin, muscle, bone) by administering (e.g., injection, transdermal administration, or embedding administration) the cell mobilizing agent of the present invention to the affected part or its surrounding part, as a result of which the tissue repair of the affected part can be promoted.

According to the present invention, since repair of biological tissues can be promoted under wide concentration range conditions of the active ingredient, side effects can be reduced as compared to conventional compounds, and deterioration of QOL can be prevented without requiring intermittent topical administration.

The cell mobilizing agent of the present invention can also be utilized for the accumulation of cells in vitro.

DESCRIPTION OF EMBODIMENTS

The cell mobilizing agent of the present invention comprises a lysophospholipid introduced with retinoic acid represented by the formula (1) and/or the formula (2) or a physiologically acceptable salt thereof as an active ingredient:

formula (2)

wherein, $R_1$ and $R_2$ are each a retinoyl group or hydrogen and are not the same with each other.

The lysophospholipid introduced with retinoic acid represented by the formula (1) and/or the formula (2) includes 1-retinoyl-sn-glycero-3-phosphocholine, 2-retinoyl-sn-glycero-3-phosphocholine, and 1-retinoyl-sn-glycero-2-phosphocholine. While the lysophospholipid introduced with retinoic acid represented by the formula (1) and/or the formula (2) contains plural structural isomers due to cis/trans isomer of the retinoyl group, either one can be used.

Examples of the steric structure of the retinoyl group include all-trans form, 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, 9,11,13-tri-cis form, and all-cis form. In the 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, and 9,11,13-tri-cis form, indication of a trans form is omitted. That is, for example, 7-cis form shows 7-cis-9,11,13-tri-trans form.

The lysophospholipid introduced with retinoic acid represented by the formula (1) and/or the formula (2) may be naturally obtained or produced by chemical synthesis. The lysophospholipid introduced with retinoic acid represented by the formula (1) and/or the formula (2) can be obtained by, for example, monoesterifying glycerophosphocholine and retinoic acid by using a condensing agent such as carbodiimide and the like, and purification by silica gel chromatography and the like. It can also be obtained by diesterifying glycerophosphocholine or lysophosphocholine and retinoic acid by using a condensing agent such as carbodiimide and the like, which is followed by regioselective hydrolysis using an enzyme such as phospholipase and the like to give a monoester form, and purification by silica gel chromatography and the like.

Examples of the physiologically acceptable salt of lysophospholipid introduced with retinoic acid represented by the formula (1) and/or the formula (2) include a salt added with an acid such as hydrochloric acid, bromic acid, sulfuric acid, nitric acid, phosphoric acid, carbonic acid, acetic acid, citric acid, butyric acid and the like, and a salt added with a base such as sodium hydroxide, potassium hydroxide, calcium hydroxide and the like.

The cell mobilizing agent of the present invention is preferably a sustained-release preparation containing a sustained release substrate.

As the sustained release substrate, a biodegradable polymer is preferable. Specific examples of the biodegradable polymer include gelatin, collagen, chitin, chitosan, hyaluronic acid, polyamino acid, polylactic acid, polyglycolic acid, a copolymer of lactic acid and glycolic acid, poly-ε-caprolactone and derivatives thereof, crosslinked forms thereof and combinations thereof. These are appropriately selected according to the sustained-release property of the object Ret-LysoPC. These may be obtained naturally or may be produced by fermentation using microorganisms or chemical synthesis.

While the derivative of the biodegradable polymer is not particularly limited, for example, those introduced with succinic acid, ethylenediamine, distearoylphosphoethanolamine and the like can be mentioned. These derivatives can be obtained by, for example, amidation, esterification and the like of the amino group, hydroxy group, carboxyl group and the like of the aforementioned compound with a biodegradable polymer side chain. These derivatives show different physical/chemical interaction with Ret-LysoPC as compared to that before derivatization, and can change the Ret-LysoPC sustained-release property from a sustained-release base material.

As the sustained release substrate, a gelatin derivative is preferable and, for example, isoelectric point 5 gelatin hydrogel, isoelectric point 9 gelatin hydrogel, succinylated gelatin hydrogel, gelatin hydrogel introduced with ethylenediamine, and gelatin hydrogel introduced with distearoylphosphoethanolamine can be mentioned.

These derivatives are appropriately selected according to the object Ret-LysoPC sustained release property (e.g., need for high concentration in the initial stage of administration and low concentration in the middle stage and thereafter and the like).

When actually administered to a living body, the effective concentration of Ret-LysoPC needs to be maintained topically. When a sustained-release base material is used, the effective concentration can be maintained for a long time by continuously releasing Ret-LysoPC. On the other hand, in a case where accumulation of a large number of cells, rather than maintenance of the concentration at a constant level, is important at the beginning of therapy, a sustained-release base material having sustained release property permitting release of a large amount of Ret-LysoPC in the initial stage of administration only needs to be selected.

While the shape of the sustained release substrate is not particularly limited, for example, cylindrical shape, prismatic shape, sheet shape, disc shape, spherical shape, paste shape and the like are available. The cylindrical shape, prismatic shape, sheet shape, and disc shape are particularly suitable for use as an embedded piece.

In the present invention, a sustained-release preparation can be obtained by, for example, adding an aqueous Ret-LysoPC solution dropwise to the above-mentioned sustained release substrate, or immersing a sustained release substrate in an aqueous Ret-LysoPC solution to impregnate the sustained release substrate with Ret-LysoPC. It can also be obtained by dissolving Ret-LysoPC in a volatile organic solvent, for example, methanol, ethanol, tetrahydrofuran, chloroform, acetone and the like, mixing same with a solution of a sustained release substrate immersed therein or a sustained release substrate dissolved therein, and evaporating the solvent.

The weight ratio of Ret-LysoPC to the sustained release substrate is generally 0.1 to 0.0001-fold. An operation for immersing the sustained release substrate in the aqueous Ret-LysoPC solution generally completes at 4-60° C. for 15 min-24 hr, during which the sustained release substrate and Ret-LysoPC form a complex by a physical/chemical interaction, whereby Ret-LysoPC is fixed on the sustained release substrate. An operation for dissolving Ret-LysoPC in a volatile organic solvent, mixing same with a solution of a sustained release substrate immersed therein or a sustained release substrate dissolved therein, and evaporating the solvent generally completes at −20 to 80° C. for 15 min-48 hr, during which the sustained release substrate and Ret-LysoPC form a complex by a physical/chemical interaction, whereby Ret-LysoPC is fixed on the sustained release substrate. These preparation methods are appropriately selected according to the sustained release substrate to be used. Physical/chemical interactions such as Coulomb force, hydrogen binding force, hydrophobic interaction and the like are considered to be involved singly or in combination in the binding of Ret-LysoPC and the sustained release base material.

The sustained-release preparation obtained above can be directly used as a transdermal administration preparation such as an adhesive preparation and the like, an embedding type preparation (transplantation carrier) in living organisms and the like, a sustained-release preparation (e.g., injection, transdermal administration preparation, embedding type preparation in living organism etc.) may also be prepared by using a pharmaceutically acceptable carrier (stabilizer, preservative, solubilizer, pH adjuster, thickener etc.) as necessary and according to a known method. As such carrier, known ones can be used. Furthermore, various additives for controlling a sustained release effect can also be added.

In the present invention, "cell mobilization" means cell migration accompanied by accumulation. The "cell mobilization" in the present invention includes both cell mobilization in vivo and cell mobilization in vitro.

The cell mobilizing agent of the present invention can be administered to human and animals (e.g., domestic animals and poultry such as bovine, horse, swine, sheep, dog, bird and the like, and experiment animals such as mouse, rat and the like) by any method such as injection, transdermal administration, embedding administration and the like. For release in a sustained manner at the object site, topical administration is preferable.

The dose of the cell mobilizing agent of the present invention can be appropriately selected such that it will be sufficient to promote tissue repair. Generally, the dose is selected from 0.1-10000 µg per an adult patient, which can be indwelled or injected at an affected part or its surrounding part. When a single administration provided only an insufficient effect, administration can also be performed plural times.

In the present invention, examples of the cells involved in the tissue repair include blood cells such as monocytes, macrophages and the like, hematopoietic stem cells and mesenchymal stem cells.

As described above, it is known that the actions of neutrophils, eosinophils, monocytes, macrophages, and the like, which are blood cells, are involved in the tissue repair processes such as wound healing, degeneration of tumor and the like (e.g., non-patent document 1). Therefore, the cell mobilizing agent of the present invention is expected to promote tissue repair by mobilizing (accumulating) the cells involved in the tissue repair in the affected part.

Since hematopoietic stem cells are stem cells that can differentiate into blood cells, they are expected to promote tissue repair when mobilized to an affected part, similar to the mobilization of blood cells.

Since mesenchymal stem cells control immune responses and change into tissues of muscle, bone and the like, they are expected to promote tissue repair when mobilized to an affected part.

The cell mobilizing agent of the present invention can be used, for example, as a therapeutic drug for damages and diseases (e.g., wound, chronic ulcer, lack of tissue, fibrosis) of tissues (e.g., skin, muscle, bone, organ), a therapeutic drug for solid cancer, a medical device (e.g., promotion of formation of endothelial tissue by transplantation material), or a vaccine (efficient antigen presentation by immunocyte mobilization).

In addition, the cell mobilizing agent of the present invention can be used for application in vitro, for example, research or medical devices (e.g., test kit, transplantation material), cell sorting reagent or medium (high purification of cells) and the like.

The amount of the cell mobilizing agent of the present invention for use in vitro can be appropriately selected such that it will be sufficient to accumulate cells.

EXAMPLES

The present invention is explained in more detail in the following by referring to Examples, Comparative Examples, Production Examples and Experimental Examples, which are not to be construed as limitative.

Representative structures of Ret-LysoPC and diretinoyl phosphocholine (hereinafter to be referred to as "Ret-PC") described in each Example and Comparative Example are shown in Table 1. In addition, retinoyl group all-trans form content percentages of Ret-LysoPC and Ret-PC, and 1-retinoyl-sn-glycero-3-phosphocholine content percentage in Ret-LysoPC were calculated according to the following descriptions, and the results are shown in Table 2. The amino group number of each gelatin derivative, which is a sustained release substrate, was determined by the TNBS method described in JP-B-4303196, and the modification ratio was calculated and shown in Table 3.

(Calculation Method of Retinoyl Group all-Trans Form Content Percentage)

The reaction product (5 mg) after purification was dissolved in 1 ml of a deuterated solvent, and $^1$H-NMR (600 MHz, internal standard TMS) was measured. Ret-LysoPC was measured using deuterated methanol, and all-trans form content percentage was calculated from the integration value (integration value 1.0 as 100%) of δ=5.8 ppm (—OCO—C$\underline{H}$=C(CH$_3$)—) signal, with the integration value of δ=1.0 ppm (—C(C$\underline{H}_3$)$_2$—) signal as 6.0. Ret-PC was measured using deuterochloroform, and all-trans form content percentage was calculated from the integration value (integration value 2.0 as 100%) of δ=5.8 ppm (—OCO—C$\underline{H}$=C(CH$_3$)—), with the integration value of δ=1.0 ppm (—C(C$\underline{H}_3$)$_2$—) signal as 12.0.

(Calculation Method of Content Percentage of 1-Retinoyl-Sn-Glycero-3-Phosphocholine in Ret-LysoPC)

The reaction product (5 mg) after purification was dissolved in 1 ml of deuterated methanol, and $^1$H-NMR (600 MHz, internal standard TMS) was measured. The 2-retinoyl-sn-glycero-3-phosphocholine content percentage was calculated from the integration value (integration value 1.0 as 100%) of δ=5.0 ppm (HO—CH$_2$—C$\underline{H}$(OCO—)—CH$_2$—O—) signal, with the integration value of δ=1.0 ppm (—C(C$\underline{H}_3$)$_2$—) signal as 6.0, as well as 1-retinoyl-sn-glycero-3-phosphocholine content percentage (100-(2-retinoyl-sn-glycero-3-phosphocholine content percentage), %) was calculated.

(Example 1) Production of Ret-LysoPC and (Comparative Example 1) Ret-PC

To all-trans retinoic acid (manufactured by Tokyo Chemical Industry Co., Ltd.) (1.0 g) were added chloroform (containing amylene) (12 g), and 1-ethyl-3-(3-dimethylaminopropyl)carbodiimide hydrochloride (0.35 g) and the mixture was stirred. After 3 hr, α-glycerophosphocholine (manufactured by Euticals S.p.A) (2.6 g) and dimethylaminopyridine (0.086 g) were added and the temperature was raised with stirring to 50° C. After 60 hr, heating was stopped, and the mixture was cooled to room temperature. While stirring the reaction solution, α-tocopherol (0.010 g) was added, and insoluble materials were filtered off. After evaporation of the solvent in the filtrate, the residue was purified by silica gel column chromatography (filler: Wakogel C-200 (manufactured by Wako Pure Chemical Industries, Ltd.) (10 g)) using chloroform, methanol, water as eluent. A fraction containing Ret-PC or a fraction containing Ret-LysoPC was divided in plurality and recovered. Each recovered fraction was passed through ion exchange resin SMN-1 (manufactured by Mitsubishi Chemical Corporation) (5.5 g), and ion exchange resin SMN-1 (manufactured by Mitsubishi Chemical Corporation) (5.5 g). Thereafter, the solvent was evaporated to give the object products (Examples 1-1-1-2 and Comparative Example 1).

The obtained object products were analyzed by $^1$H-NMR (600 MHz, deuterated methanol, internal standard TMS), and the presence of Ret-LysoPC was confirmed from δ=1.0 ppm (6H, s, —C(C$\underline{H}_3$)$_2$—), 1.5 ppm (2H, m, —C(CH$_3$)$_2$—CH$_2$—CH$_2$—C$\underline{H}_2$—), 1.6 ppm (2H, m, —C(CH$_3$)$_2$—CH$_2$—C$\underline{H}_2$—CH$_2$—), 1.7 ppm (3H, s, —CH$_2$—C(C$\underline{H}_3$)═), 2.0 ppm (3H, s, —OCO—CH═C(CH$_3$)—CH═CH—CH═C(C$\underline{H}_3$)—), 2.0 ppm (2H, m, —C(CH$_3$)$_2$—C$\underline{H}_2$—CH$_2$—CH$_2$—) r, 2.3 ppm (3H, s, —OCO—CH═C(C$\underline{H}_3$)—CH═CH—CH═C(CH$_3$)—), 3.2 ppm (9H, s, N(C$\underline{H}_3$)$_3$—CH$_2$—CH$_2$), 3.6 ppm (2H, m, N(CH$_3$)$_3$—C$\underline{H}_2$—CH$_2$—) r, 3.9 ppm (2H, m, N(CH$_3$)$_3$—CH$_2$—CH$_2$—O—POO—O—C$\underline{H}_2$—), 4.0 ppm (1H, m, —CH$_2$—C$\underline{H}$(OH)—CH$_2$—OCO—CH═), 4.1, 4.2 ppm (2H, m, —C$\underline{H}_2$—OCO—CH═), 4.3 ppm (2H, m, N(CH$_3$)$_3$—CH$_2$—C$\underline{H}_2$—), 5.0-7.8 ppm (6H, m, —OCO—C$\underline{H}$═C(CH$_3$)—C$\underline{H}$═C$\underline{H}$—C$\underline{H}$═C(CH$_3$)—C$\underline{H}$═C$\underline{H}$—).

The obtained object products were analyzed by $^1$H-NMR (600 MHz, deuterochloroform, internal standard TMS), and the presence of Ret-PC was confirmed from δ=1.0 ppm (12H, s, —C(C$\underline{H}_3$)$_2$—) r, 1.5 ppm (4H, m, —C(CH$_3$)2-CH$_2$—C$\underline{H}_2$—CH$_2$—), 1.6 ppm (4H, m, —C(CH$_3$)$_2$—CH$_2$—C$\underline{H}_2$—CH$_2$—), 1.7 ppm (6H, s, —CH$_2$—C(C$\underline{H}_3$)═), 2.0 ppm (6H, s, —OCO—CH═C(CH$_3$)—CH═CH—CH═C(C$\underline{H}_3$)—), 2.0 ppm (4H, m, —C(CH$_3$)$_2$—C$\underline{H}_2$—CH$_2$—CH$_2$—), 2.3 ppm (6H, s, —OCO—CH═C(C$\underline{H}_3$)—CH═CH—CH═C(CH$_3$)—), 3.3 ppm (9H, s, N(C$\underline{H}_3$)$_3$—CH$_2$—CH$_2$), 3.8 ppm (2H, m, N(CH$_3$)$_3$—C$\underline{H}_2$—CH$_2$—), 4.0 ppm (2H, m, N(CH$_3$)$_3$—CH$_2$—CH$_2$—O—POO—O—C$\underline{H}_2$—), 4.3, 4.4 ppm (2H, m, —C$\underline{H}_2$—OCO—CH═), 4.3 ppm (2H, br, N(CH$_3$)$_3$—CH$_2$—C$\underline{H}_2$—), 5.3 ppm (1H, m, —CH$_2$—C$\underline{H}$(OCO—CH═)—CH$_2$—OCO—CH═), 5.0-7.8 ppm (12H, m, —OCO—C$\underline{H}$═C(CH$_3$)—C$\underline{H}$═C$\underline{H}$—C$\underline{H}$═C(C$\underline{H}_3$)—CH═C$\underline{H}$—).

(Example 2) Production of Ret-LysoPC

To all-trans retinoic acid (manufactured by Tokyo Chemical Industry Co., Ltd.) (0.60 g) were added chloroform (containing amylene) (18 g), and 1-ethyl-3-(3-dimethylaminopropyl)carbodiimide hydrochloride (0.21 g), and the mixture was stirred. After 3 hr, the solvent was evaporated to give a concentrated product (2.0 g). α-glycerophosphocholine (manufactured by Euticals S.p.A) (0.083 g) and dimethylaminopyridine (0.053 g) were added and the temperature was raised with stirring to 50° C. After 30 hr, heating was stopped, and the mixture was cooled to room temperature. While stirring the reaction solution, α-tocopherol (0.006 g) was added, and insoluble materials were filtered off. After evaporation of the solvent in the filtrate, the residue was purified by silica gel column chromatography (filler: Wakogel C-200 (manufactured by Wako Pure Chemical Industries, Ltd.) (3.0 g)) using chloroform, methanol, water as eluent. A fraction containing Ret-LysoPC was recovered, and passed through ion exchange resin SMN-1 (manufactured by Mitsubishi Chemical Corporation) (3.3 g), and ion exchange resin SMN-1 (manufactured by Mitsubishi Chemical Corporation) (3.3 g). Thereafter, the solvent was evaporated to give the object products.

The obtained object products were analyzed by $^1$H-NMR (600 MHz, deuterated methanol, internal standard TMS), and the presence of Ret-LysoPC was confirmed from δ=1.0 ppm (6H, s, —C(C$\underline{H}_3$)$_2$—), 1.5 ppm (2H, m, —C(CH$_3$)$_2$—CH$_2$—CH$_2$—C$\underline{H}_2$—), 1.6 ppm (2H, m, —C(CH$_3$)$_2$—CH$_2$—C$\underline{H}_2$—CH$_2$—), 1.7 ppm (3H, s, —CH$_2$—C(C$\underline{H}_3$)═), 2.0 ppm (3H, s, —OCO—CH═C(CH$_3$)—CH═CH—CH═C(C$\underline{H}_3$)—), 2.0 ppm (2H, m, —C(CH$_3$)$_2$—C$\underline{H}_2$—CH$_2$—CH$_2$—), 2.3 ppm (3H, s, —OCO—CH═C(C$\underline{H}_3$)—CH═CH—CH═C(CH$_3$)—), 3.2 ppm (9H, s, N(C$\underline{H}$3)$_3$—CH$_2$—CH$_2$), 3.6 ppm (2H, m, N(CH$_3$)$_3$—C$\underline{H}_2$—CH$_2$—), 3.9 ppm (2H, m, N(CH$_3$)$_3$—CH$_2$—CH$_2$—O—POO—O—C$\underline{H}_2$—), 4.0 ppm (1H, m, —CH$_2$—C$\underline{H}$(OH)—CH$_2$—OCO—CH═), 4.1, 4.2 ppm (2H, m, —C$\underline{H}_2$—OCO—CH═), 4.3 ppm (2H, m, N(CH$_3$) 3-CH$_2$—C$\underline{H}_2$—), 5.0-7.8 ppm (6H, m, —OCO—C$\underline{H}$═C(CH$_3$)—C$\underline{H}$═C$\underline{H}$—C$\underline{H}$═C(CH$_3$)—CH═C$\underline{H}$—).

TABLE 1

| name of compound | structural formula |
|---|---|
| Ret-LysoPC | (structural formula shown) |

TABLE 1-continued

| name of compound | structural formula |
|---|---|
| Ret-PC | (structure shown) |

TABLE 2

| name of compound | retinoyl group all-trans form content percentage (%) | 1-retinoyl-sn-glycero-3-phosphocholine content percentage (%) |
|---|---|---|
| Example 1-1 | Ret-LysoPC | 23 | 93 |
| Example 1-2 | Ret-LysoPC | 87 | 92 |
| Comparative Example 1 | Ret-PC | 71 | — |
| Example 2 | Ret-LysoPC | 72 | 90 |

(Example 3) Evaluation of Monocyte Mobilization Effect by Ret-LysoPC

Figure 1:
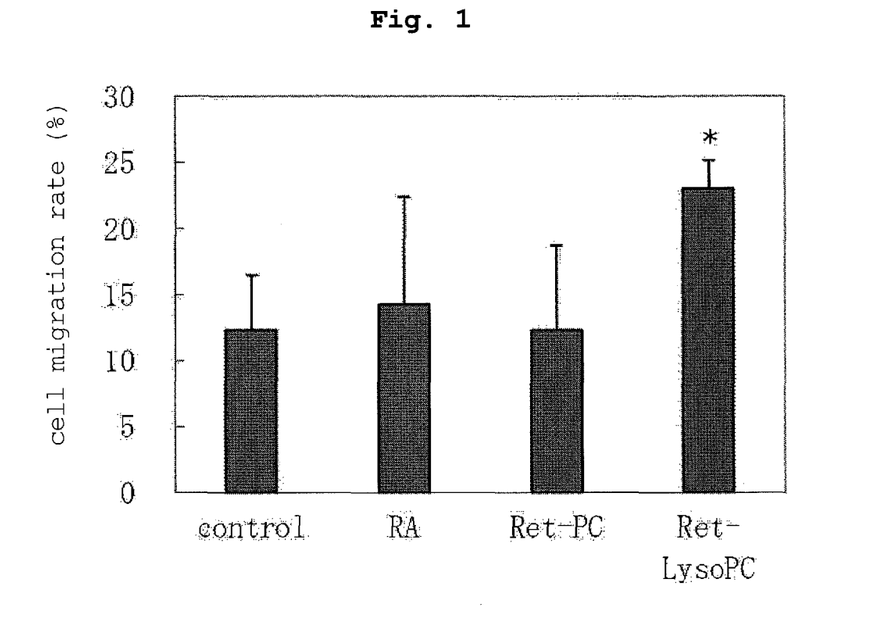
FIG. 1 is a graph showing a monocyte mobilization effect by Ret-LysoPC. A significant difference from the control was detected, and shown as *: $P<0.05$.

A cell suspension of human acute monocytic leukaemia cell line (hereinafter to be referred to as "THP-1") (manufactured by ATCC) was centrifuged, the supernatant was discarded, 0.1% bovine serum albumin (fatty acid-free, manufactured by SIGMA ALDRICH)-containing RPMI-1640 (manufactured by Life Technologies) was added to give a dispersion. It was centrifuged again, the supernatant was discarded to give cell pellets. 0.1% Bovine serum albumin-containing RPMI-1640 was added to adjust the cell density to $1\times10^6$ cells/ml. The cell suspension (100 µl/well) was added to Transwell (manufactured by Corning Incorporated, φ6.5 mm, pore size φ8.0 µm). The cells were incubated at 37° C., 5% $CO_2$ for 30 min, and a measurement solution (all-trans retinoic acid (manufactured by Tokyo Chemical Industry Co., Ltd.) (hereinafter to be referred to as "RA"), Ret-PC of Comparative Example 1 or Ret-LysoPC of Example 1-2 dissolved in 0.1% bovine serum albumin-containing RPMI-1640 to 10 nM, and 0.1% bovine serum albumin-containing RPMI-1640 alone) was placed in the lower part of the multiple well plate (600 µl/well). After incubation at 37° C., 5% $CO_2$ for 3 hr, the cell suspension in the multiple well plate was collected, cell density was measured by a hemacytometer and the cell migration rate was determined. The cell migration rate was defined as follows.

cell migration rate (%)=(number of cells in multiple well plate)/(number of cells added to Transwell)

The measurement results of the cell migration rate of each measurement solution are shown in FIG. 1. The control refers to 0.1% bovine serum albumin-containing RPMI-1640 with no addition. RA (10 nM), Ret-PC (10 nM) did not show cell migration, and was free of monocyte mobilization effect, whereas Ret-LysoPC (10 nM) showed significant (P<0.05) cell migration as compared to the control. Thus, it was found that Ret-LysoPC has a monocyte mobilization effect.

Figure 2:
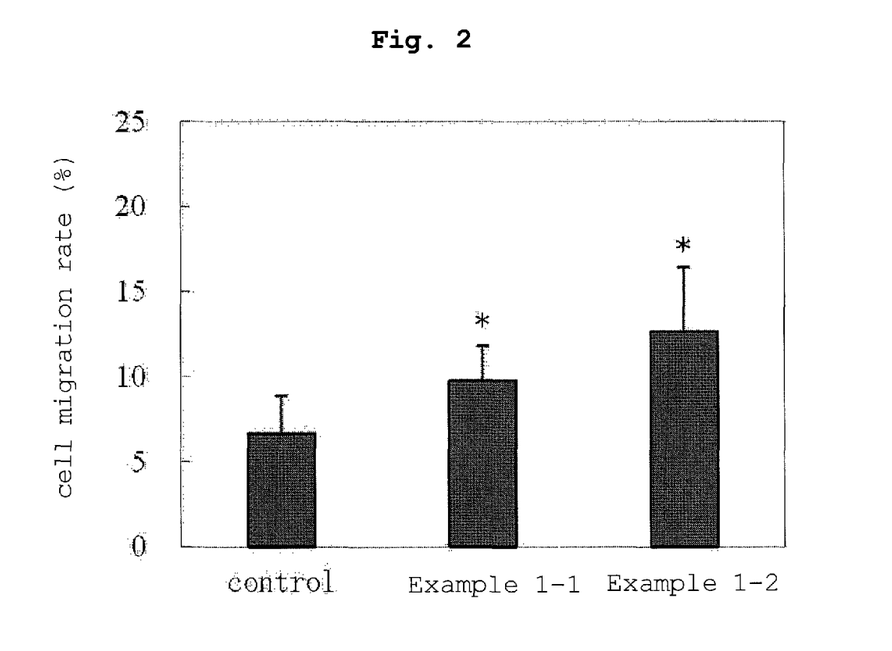
FIG. 2 is a graph showing an influence of the content of retinoyl group isomer in Ret-LysoPC on the monocyte mobilization effect. A significant difference from the control was detected, and shown as *: $P<0.05$.

(Example 4) Evaluation of Influence on Monocyte Mobilization Effect by Retinoyl Group all-Trans Form Content Percentage A cell suspension of THP-1 was centrifuged, the supernatant was discarded, 0.1% bovine serum-containing RPMI-1640 was added to give a dispersion. It was centrifuged again, the supernatant was discarded to give cell pellets. 0.1% Bovine serum albumin-containing RPMI-1640 was added to adjust the cell density to $1\times10^6$ cells/ml. The cell suspension (100 µl/well) was added to Transwell (manufactured by Corning Incorporated, φ6.5 mm, pore size φ8.0 µm). The cells were incubated at 37° C., 5% $CO_2$ for 30 min, and a measurement solution (Ret-LysoPC of Examples 1-1 and 1-2 dissolved in 0.1% bovine serum albumin-containing RPMI-1640 to 10 nM, and 0.1% bovine serum albumin-containing RPMI-1640 alone) was placed in the lower part of the multiple well plate (600 µl/well). After incubation at 37° C., 5% $CO_2$ for 3 hr, the cell suspension in the multiple well plate was collected, cell density was measured by a hemacytometer and the cell migration rate was determined.

The measurement results of the cell migration rate of each measurement solution are shown in FIG. 2. The control refers to 0.1% bovine serum albumin-containing RPMI-1640 with no addition. Cell migration was confirmed in any Ret-LysoPC (10 nM). One having a high all-trans form content percentage tends to show a high monocyte mobilization effect. However, significant migration of cell was confirmed even in one having a low all-trans form content percentage, and other isomers were also suggested to have a monocyte mobilization effect.

Figure 3:
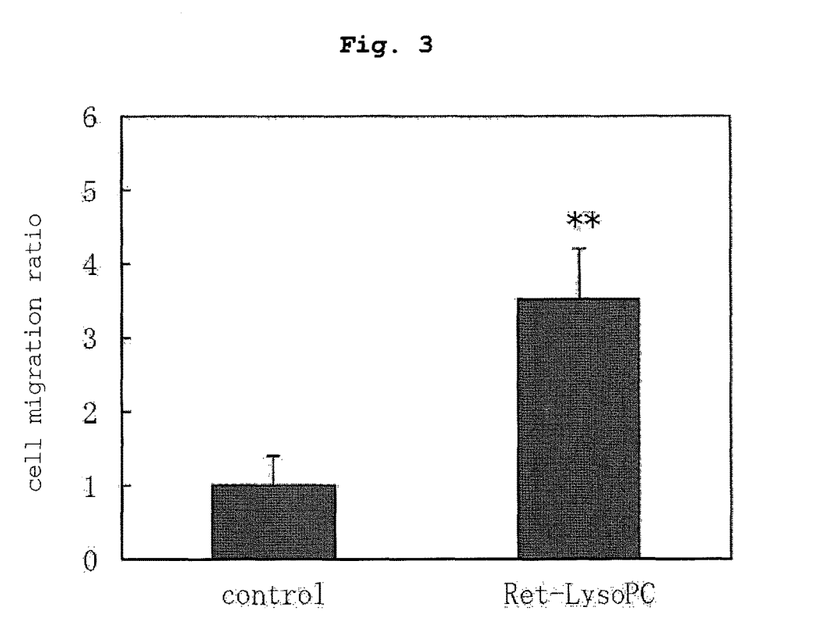
FIG. 3 is a graph showing a mesenchymal stem cell mobilization effect by Ret-LysoPC. A significant difference from the control was detected, and shown as **: $P<0.01$.

(Example 5) Evaluation of Mesenchymal Stem Cell Mobilization Effect by Ret-LysoPC Human bone marrow-derived mesenchymal stem cell line (UE7T-13) (manufactured by National Institute of Biomedical Innovation JCRB Cell Bank) was previously cultured in serum-free DMEM (manufactured by SIGMA ALDRICH) for 24 hr, and 0.25% trypsin/1 mM EDTA solution (manufactured by SIGMA ALDRICH) was added to give a dispersion. 10% Serum-containing DMEM (Powered by 10 medium; manufactured by GlycoTechnica Ltd.) was added, the cell suspension was centrifuged, the supernatant was discarded, 0.1% bovine serum albumin (fatty acid-free, manufactured by SIGMA ALDRICH)-containing DMEM (manufactured by SIGMA ALDRICH) was added to give a dispersion. It was centrifuged again, the supernatant was discarded to give cell pellets. 0.1% Bovine serum albumin-containing DMEM was added to adjust the cell density to $4\times10^5$ cells/ml. The cell suspension (100 µl/well) was added to Transwell (manufactured by Corning Incorporated, φ6.5 mm, pore size φ8.0 µm). The cells were incubated at 37° C., 5% $CO_2$ for 30 min, and a measurement solution (Ret-LysoPC of Example 1-2 dissolved in 0.1% bovine serum albumin-containing DMEM to 10 nM, or 0.1% bovine serum albumin-containing DMEM alone) was placed in the lower part of the multiple well plate (600 µl/well). After incubation at 37° C., 5% $CO_2$ for 4 hr, the supernatant in the insert was removed. The cells on the upper membrane side were removed, the cells on the lower membrane side were immobilized with 4% para-formaldehyde solution, and stained with crystalviolet solution. They were washed with water, dried, and the number of cells per one field was measured by microscopic observation. The cell migration ratio was defined as follows.

cell migration ratio=(number of cell per one membrane field when each measurement solution was used)/(number of cells per one membrane field of control)

The control refers to 0.1% bovine serum albumin-containing DMEM with no addition.

The measurement results of cell migration ratio in each measurement solution are shown in FIG. 3. Ret-LysoPC (10 nM) showed a significant cell migration as compared to the control ($P<0.01$). Thus, it was found that Ret-LysoPC has a mesenchymal stem cell mobilization effect.

(Production Example 1) Production of Gelatin Hydrogel-Dried Product

As a sustained release substrate of Ret-LysoPC, a gelatin hydrogel-dried product shown below was produced, and used for the sustained release test shown in Example 5.

isoelectric point 5 gelatin hydrogel-dried product (hereinafter to be referred to as "pI5 gel".)
isoelectric point 9 gelatin hydrogel-dried product (hereinafter to be referred to as "pI9 gel".)
succinylated gelatin hydrogel-dried product (hereinafter to be referred to as "Suc gel".)
gelatin hydrogel-dried product introduced with ethylenediamine (hereinafter to be referred to as "E50 gel".)
gelatin hydrogel-dried product introduced with distearoylphosphoethanolamine (hereinafter to be referred to as "DSPE gel".)

(Production Example 1-1) Production of Succinylated Gelatin

Gelatin with isoelectric point 5 (derived from beef bones, average molecular weight about 100,000: manufactured by Nitta Gelatin Inc.) (1.0 g) was dissolved in dimethyl sulfoxide (14 g). Succinic anhydride (0.014 g) was dissolved in dimethyl sulfoxide (4.5 g), the solution was added to a gelatin solution. After stirring at 37° C. for 1 hr, the mixture was wrapped with a dialysis membrane, and dialyzed for 3 days using water as an outer phase. After completion of the dialysis, the internal phase was recovered, and lyophilized to give succinylated gelatin. The modification ratio of the gelatin is shown in Table 3.

(Production Example 1-2) Production of Cationized Gelatin

Gelatin with isoelectric point 9 (derived from pig skin, average molecular weight about 100,000: manufactured by Nitta Gelatin Inc.) (1.0 g) was dissolved in 24 ml of 0.1 M aqueous phosphate buffer (pH 5.0). Then, 50 equivalent amount of ethylenediamine was added relative to the carboxyl group of gelatin, the pH of the solution was adjusted to 5.0 with 11 M aqueous hydrochloric acid solution. Then, 3 equivalent amount of 1-ethyl-3-(3-dimethylaminopropyl) carbodiimide hydrochloride was added relative to the carboxyl group of gelatin, and 0.1 M aqueous phosphate buffer (pH 5.0) was added to adjust the final concentration of gelatin to 2 wt %. After stirring at 37° C. for 4 hr, the reaction product was wrapped with a dialysis membrane, and dialyzed for 3 days using water as an outer phase. After completion of the dialysis, the internal phase was recovered, and lyophilized to give cationized gelatin. The modification ratio of the gelatin is shown in Table 3.

(Production Example 1-3) Production of Gelatin Introduced with Distearoylphosphoethanolamine Gelatin with isoelectric point 5 (derived from beef bones, average molecular weight about 100,000: manufactured by Nitta Gelatin Inc.) (1.0 g) was dissolved in dimethyl sulfoxide (30 g). N-(succinimidyloxyglutaryl)-phosphoethanolamine, distearoyl (COATSOME FE-8080SU5; manufactured by NOF CORPORATION) (0.67 g) was added, and the mixture was stirred at 25° C. for 18 hr. The reaction mixture was wrapped with a dialysis membrane, and dialyzed for 3 days using water as an outer phase. After completion of the dialysis, the internal phase was recovered, and lyophilized to give gelatin introduced with distearoylphosphoethanolamine. The modification ratio of the gelatin is shown in Table 3.

TABLE 3

| | name of compound | modification ratio (%) |
|---|---|---|
| Production Example 1-1 | succinylated gelatin | 30 |
| Production Example 1-2 | cationized gelatin | 50 |
| Production Example 1-3 | gelatin introduced with distearoylphosphoethanolamine | 15 |

(Production Example 1-4) Production of Hydrogel-Dried Product

Succinylated gelatin (0.5 g) produced in Production Example 1-1 was dissolved in water (9.5 g), and the pH of the solution was adjusted to 5.0 with 5 M aqueous sodium hydroxide solution. 25% Aqueous glutaraldehyde solution (45 µl) was added, and the mixture was gently stirred for 30 seconds. Then, the reaction mixture was dispensed, shaded, stood at room temperature for 30 min, and a crosslinking reaction was performed at 4° C. for 12 hr. The gel was cast in 0.1 M aqueous glycine solution (500 ml), and the mixture was shaken at room temperature for 1 hr to discontinue the crosslinking reaction. Then, the aqueous glycine solution was substituted by pure water, and the mixture was shaken at room temperature for 1 hr, which was repeated 3 times. The obtained hydrogel was lyophilized to give Suc gel.

Other gelatins were also crosslinked and purified by a similar method, and pI5 gel was obtained from gelatin with isoelectric point 5 (derived from beef bones, average molecular weight about 100,000 by Nitta Gelatin Inc.), pI9 gel was obtained from gelatin with isoelectric point 9 (derived from pig skin, average molecular weight about 100,000: manufactured by Nitta Gelatin Inc.), E50 gel was obtained from the gelatin derivative of Production Example 1-2, and DSPE gel was obtained from the gelatin derivative of Production Example 1-3.

(Example 6) Sustained Release Test of Ret-LysoPC-Containing Gelatin Hydrogel

As one embodiment of a sustained-release preparation, a Ret-LysoPC-containing sustained-release preparation using a gelatin derivative as a sustained release substrate was produced, and a sustained release test was performed. That is, various gelatin hydrogel-dried products shown in Production Example 1 as sustained release substrates were impregnated with aqueous Ret-LysoPC solution, and the sustained release property in phosphate buffered saline (pH 7.4, hereinafter to be referred to as "PBS") and 10 µg/ml collagenase-containing PBS was evaluated.

Ret-LysoPC (Example 1-2) was dissolved in PBS such that Ret-LysoPC concentration was 500 µM. The 500 µM aqueous Ret-LysoPC solution (100 µl) was added dropwise to gelatin hydrogel (10 mg), and the hydrogel was impregnated with the solution at 37° C. for 1 hr. PBS (500 µl) was added, and the mixture was stood at 37° C. under shading conditions for a given time (start of sustained release test). Thereafter, the mixture was centrifuged at 4° C., 5000 rpm for 10 min, the total amount of the supernatant was recovered and fresh PBS (500 µl) was added. This operation was repeated predetermined number of times. After 12 hr from the start of the sustained release test, the supernatant was recovered. In the tests using Suc gel, E50 gel, DSPE gel, 10 µg/ml collagenase L (manufactured by Nitta Gelatin Inc.)-containing PBS (500 µl) was added, and the mixture was similarly stood for a given time. Similarly, the supernatant was recovered, and fresh 10 µg/ml collagenase L-containing PBS (500 µl) was added. This operation was repeated until the sustained release substrate disappeared, or for 60 hr from the start of the sustained release test. The concentration of Ret-LysoPC in the recovered supernatant was measured by reversed-phase HPLC and the sustained release rate of Ret-LysoPC was determined.

Figure 4:
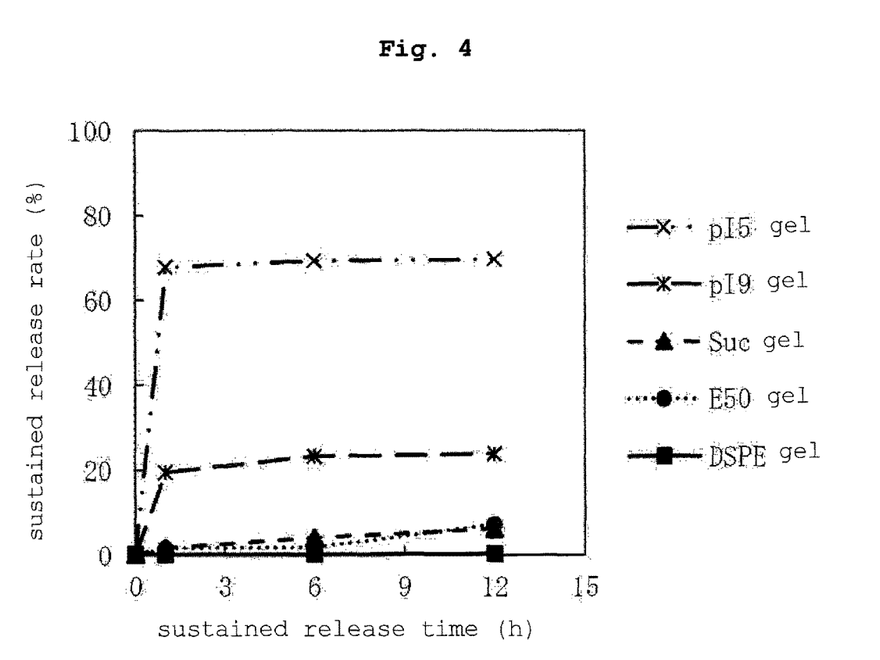
FIG. 4 is a graph showing sustained release of Ret-LysoPC from a sustained-release preparation containing Ret-LysoPC.
Figure 5:
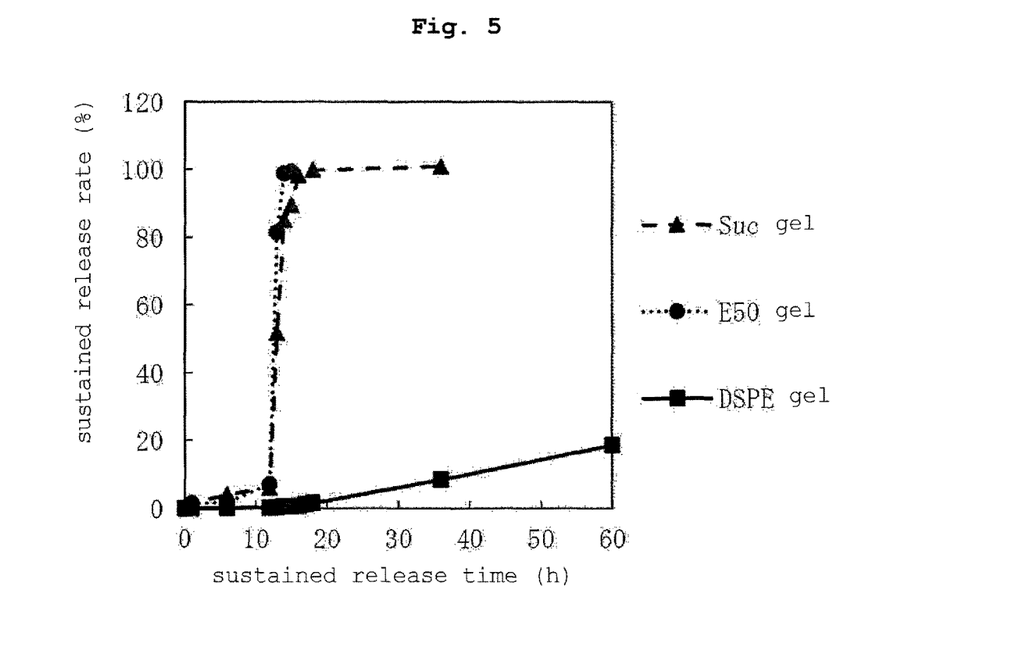
FIG. 5 is a graph showing sustained release of Ret-LysoPC associated with the decomposition of the sustained release substrate.

FIG. 4 and FIG. 5 show the sustained release rate of Ret-LysoPC at each recovery time. It was found that the sustained release property of Ret-LysoPC varied greatly depending on the kind of gelatin. This is because interactions with the sustained release substrate and Ret-LysoPC are different. It was confirmed that Ret-LysoPC was released in a sustained manner along with the decomposition of the sustained release substrate by the addition of collagenase.

Figure 6:
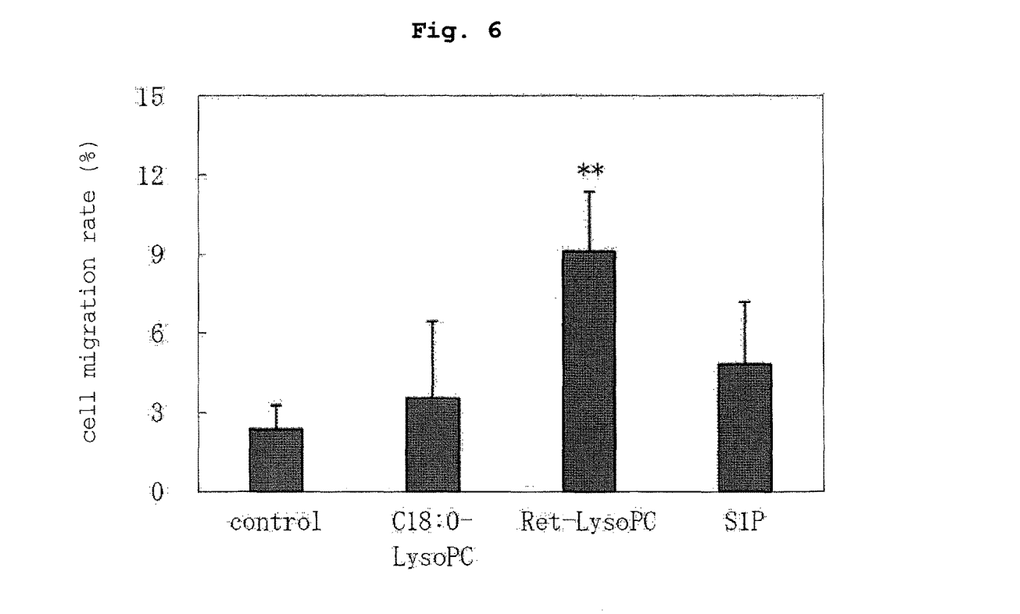
FIG. 6 is a graph showing comparison of a monocyte mobilization effect of Ret-LysoPC, C18:0-LysoPC and S1P each at 100 nM. A significant difference from the control was detected, and shown as **: $P<0.01$.
Figure 7:
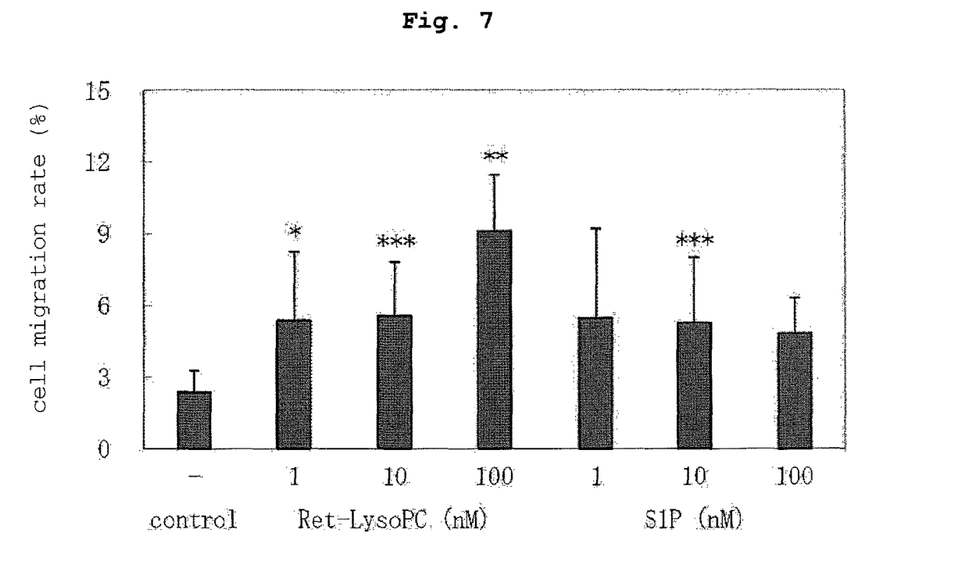
FIG. 7 is a graph showing comparison of the concentration dependency of a monocyte mobilization effect of Ret-LysoPC and S1P. A significant difference from the control was detected, and shown as *: $P<0.05$, : $P<0.01$, *: $P<0.001$.

(Experimental Example 1) Comparison Test of Monocyte Mobilization Effect of Each Lysophospholipid Using human acute monocytic leukaemia cell line (THP-1) (manufactured by ATCC), a monocyte migration effect of each sample was evaluated. A cell suspension of THP-1 was centrifuged, the supernatant was discarded, 0.1% bovine serum-containing RPMI-1640 was added to give a dispersion. It was centrifuged again, the supernatant was discarded to give cell pellets. 0.1% Bovine serum albumin-containing RPMI-1640 was added to adjust the cell density to $1 \times 10^6$ cells/ml. The cell suspension (100 µl/well) was added to Transwell (manufactured by Corning Incorporated, φ6.5 mm, pore size φ8.0 µm). The cells were incubated at 37° C., 5% $CO_2$ for 30 min, and a measurement solution (C18:0-LysoPC (COATSOME MC-80H; manufactured by NOF CORPORATION), Ret-LysoPC of Example 2 or S1P (manufactured by Toronto Research Chemicals) dissolved in 0.1% bovine serum albumin-containing RPMI-1640, and 0.1% bovine serum albumin-containing RPMI-1640 alone) was placed in the lower part of the multiple well plate (600 l/well). After incubation at 37° C., 5% $CO_2$ for 3 hr, the cell suspension in the multiple well plate was collected, cell density was measured by a hemacytometer and the cell migration rate was determined.

The measurement results of the cell migration rate of each measurement solution are shown in FIG. 6 and FIG. 7. The control refers to 0.1% bovine serum albumin-containing RPMI-1640 with no addition. From FIG. 6, it is clear that a monocyte mobilization effect is absent in C18:0-LysoPC (100 nM), but present in Ret-LysoPC (100 nM). Also, it was clarified from FIG. 7 that S1P did not show a significant ($p<0.05$) monocyte mobilization effect at 1, 100 nM, but Ret-LysoPC showed a significant monocyte mobilization effect at any of 1-100 nM.

Figure 8:
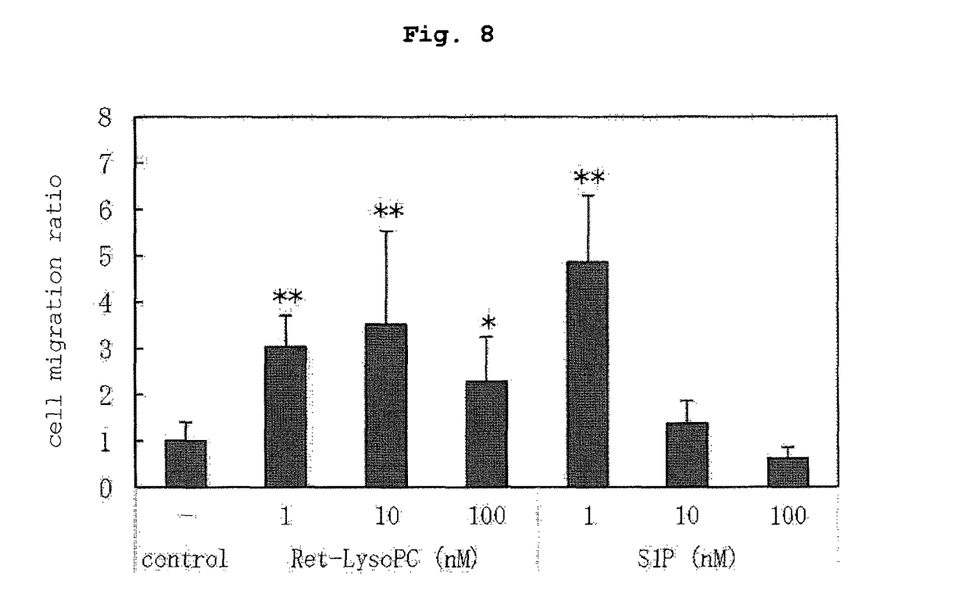
FIG. 8 is a graph showing comparison of the concentration dependency of a mesenchymal stem cell mobilization effect of Ret-LysoPC and SIP. A significant difference from the control was detected, and shown as *: $P<0.05$, **: $P<0.01$.

(Experimental Example 2) Comparison Test of Mesenchymal Stem Cell Mobilization Effect of Each Lysophospholipid Human bone marrow-derived mesenchymal stem cell line (UE7T-13) (manufactured by National Institute of Biomedical Innovation JCRB Cell Bank) was previously cultured in serum-free DMEM (manufactured by SIGMA ALDRICH) for 24 hr, and 0.25% trypsin/1 mM EDTA solution (manufactured by SIGMA ALDRICH) was added to give a dispersion. 10% Serum-containing DMEM (Powered by 10 medium; manufactured by GlycoTechnica Ltd.) was added, the cell suspension was centrifuged, the supernatant was discarded, 0.1% bovine serum albumin (fatty acid-free, manufactured by SIGMA ALDRICH)-containing DMEM (manufactured by SIGMA ALDRICH) was added to give a dispersion. It was centrifuged again, the supernatant was discarded to give cell pellets. 0.1% Bovine serum albumin-containing DMEM was added to adjust the cell density to $4 \times 10^5$ cells/ml. The cell suspension (100 µl/well) was added to Transwell (manufactured by Corning Incorporated, φ6.5 mm, pore size φ8.0 µm). The cells were incubated at 37° C., 5% $CO_2$ for 30 min, and a measurement solution (Ret-LysoPC of Example 1-2 or S1P (manufactured by Toronto Research Chemicals) dissolved in 0.1% bovine serum albumin-containing DMEM to a given concentration, and 0.1% bovine serum albumin-containing DMEM alone) was placed in the lower part of the multiple well plate (600 l/well). After incubation at 37° C., 5% $CO_2$ for 4 hr, the supernatant in the insert was removed. The cells on the upper membrane side were removed, the cells on the lower membrane side were immobilized with 4% para-formaldehyde solution, and stained with crystal violet solution. They were washed with water, dried, and the number of cells per one field was measured by microscopic observation. The cell migration ratio was defined as follows.

cell migration ratio=(number of cell per one membrane field when each measurement solution was used)/(number of cells per one membrane field of control)

The control refers to 0.1% bovine serum albumin-containing DMEM with no addition.

The measurement results of cell migration ratio in each measurement solution are shown in FIG. 8. It was clarified from FIG. 8 that SIP did not show a significant ($p<0.05$) mesenchymal stem cell mobilization effect at 10, 100 nM, but Ret-LysoPC showed a significant mesenchymal stem cell mobilization effect at any of 1-100 nM.

This application is based on patent application No. 2014-128644 filed in Japan, the contents of which are encompassed in full herein.

The invention claimed is:

1. A cell mobilizing agent comprising a lysophospholipid introduced with retinoic acid represented by the formula (1) and/or the formula (2) or a physiologically acceptable salt thereof as an active ingredient:

wherein, $R_1$ and $R_2$ are each a retinoyl group or hydrogen and are not the same with each other.

2. The cell mobilizing agent according to claim 1, wherein the retinoyl group is all-trans form, 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, 9,11,13-tri-cis form or all-cis form.

3. The cell mobilizing agent according to claim 1, which is for promoting biological tissue repair by cell mobilization.

4. The cell mobilizing agent according to claim 1, wherein the cell to be mobilized is a blood cell, a hematopoietic stem cell or a mesenchymal stem cell.

5. The cell mobilizing agent according to claim 1, which is a sustained-release preparation comprising a sustained release substrate.

6. The cell mobilizing agent according to claim 5, wherein the sustained release substrate is a biodegradable polymer.

7. The cell mobilizing agent according to claim 6, wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof and crosslinked forms thereof.

8. The cell mobilizing agent according to claim 2, which is for promoting biological tissue repair by cell mobilization.

9. The cell mobilizing agent according to claim 8, wherein the cell to be mobilized is a blood cell, a hematopoietic stem cell or a mesenchymal stem cell.

10. The cell mobilizing agent according to claim 9, which is a sustained-release preparation comprising a sustained release substrate.

11. The cell mobilizing agent according to claim 10, wherein the sustained release substrate is a biodegradable polymer.

12. The cell mobilizing agent according to claim 11, wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof and crosslinked forms thereof.

* * * * *

UNITED STATES PATENT AND TRADEMARK OFFICE
CERTIFICATE OF CORRECTION

PATENT NO. : 10,092,582 B2
APPLICATION NO. : 15/320695
DATED : October 9, 2018
INVENTOR(S) : Yasuhiko Tabata et al.

Page 1 of 2

It is certified that error appears in the above-identified patent and that said Letters Patent is hereby corrected as shown below:

In the Claims

Claims 1-12 at Column 17, Line 7, through Column 18, Line 36, should be deleted and replaced with:

1. A method of mobilizing a cell comprising administering a lysophospholipid introduced with retinoic acid represented by the formula (1) and/or the formula (2) or a physiologically acceptable salt thereof as an active ingredient to a subject in need thereof:

formula (1)

formula (2)

wherein, $R_1$ and $R_2$ are each a retinoyl group or hydrogen and are not the same with each other.

Signed and Sealed this
Twenty-sixth Day of March, 2019

Andrei Iancu
*Director of the United States Patent and Trademark Office*

2. The method according to claim 1, wherein the retinoyl group is all-trans form, 7-cis form, 9-cis form, 11-cis form, 13-cis form, 7,9-di-cis form, 7,11-di-cis form, 7,13-di-cis form, 9,11-di-cis form, 9,13-di-cis form, 11,13-di-cis form, 7,9,11-tri-cis form, 7,9,13-tri-cis form, 7,11,13-tri-cis form, 9,11,13-tri-cis form or all-cis form.

3. The method according to claim 1, wherein the method promotes biological tissue repair by cell mobilization.

4. The method according to claim 1, wherein the cell is a blood cell, a hematopoietic stem cell, or a mesenchymal stem cell.

5. The method according to claim 1, wherein a sustained-release cell mobilizing agent comprising the lysophospholipid introduced with retinoic acid represented by formula (1) and/or formula (2) or a physiologically acceptable salt thereof, and a sustained release substrate is administered to the subject.

6. The method according to claim 5, wherein the sustained release substrate is a biodegradable polymer.

7. The method according to claim 6, wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof, and crosslinked forms thereof.

8. The method according to claim 2, wherein the method promotes biological tissue repair by cell mobilization.

9. The method according to claim 8, wherein the cell is a blood cell, a hematopoietic stem cell, or a mesenchymal stem cell.

10. The method according to claim 9, wherein a sustained-release mobilizing agent comprising the lysophospholipid introduced with retinoic acid represented by formula (1) and/or formula (2) or a physiologically acceptable salt thereof, and a sustained release substrate is administered to the subject.

11. The method according to claim 10, wherein the sustained release substrate is a biodegradable polymer.

12. The method according to claim 11, wherein the biodegradable polymer is one or more kinds of biodegradable polymers selected from the group consisting of gelatin, collagen, chitin, chitosan, hyaluronic acid, polyamino acid, polylactic acid, polyglycolic acid, a copolymer of lactic acid and glycolic acid, poly-ε-caprolactone, derivatives thereof, and crosslinked forms thereof.